US008908829B2

(12) United States Patent
Watanabe et al.

(10) Patent No.: US 8,908,829 B2
(45) Date of Patent: Dec. 9, 2014

(54) X-RAY IMAGING APPARATUS AND X-RAY IMAGING METHOD

(75) Inventors: Masatoshi Watanabe, Isehara (JP); Taihei Mukaide, Yokohama (JP); Kazuhiro Takada, Kawasaki (JP); Kazunori Fukuda, Fujisawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 289 days.

(21) Appl. No.: 13/581,498

(22) PCT Filed: Feb. 23, 2011

(86) PCT No.: PCT/JP2011/054667
§ 371 (c)(1), (2), (4) Date: Aug. 28, 2012

(87) PCT Pub. No.: WO2011/108555
PCT Pub. Date: Sep. 9, 2011

(65) Prior Publication Data

US 2012/0321042 A1 Dec. 20, 2012

(30) Foreign Application Priority Data

Mar. 5, 2010 (JP) ................................ 2010-049313

(51) Int. Cl.
*G01T 1/20* (2006.01)
*G01N 23/02* (2006.01)
*G01T 1/00* (2006.01)
*A61B 6/00* (2006.01)

(52) U.S. Cl.
CPC ............ *G01T 1/00* (2013.01); *G01N 2223/505* (2013.01); *G01N 2223/646* (2013.01); *G01N 23/02* (2013.01)
USPC ........ 378/62; 378/98.8; 250/370.11; 250/367

(58) Field of Classification Search
CPC ........... A61B 6/00; A61B 6/48; A61B 6/484; A61B 6/485; G01N 23/02; G01N 23/04; G01N 23/043; G01N 23/083; G01N 23/087; G01N 2223/505; G03B 42/02; G21K 4/00; G21K 2004/00; G01T 1/20; G01T 1/2006; G01T 1/362
USPC ...................... 378/62, 98.8; 250/370.11, 367
See application file for complete search history.

(56) References Cited

U.S. PATENT DOCUMENTS

| | | | | |
|---|---|---|---|---|
| 4,686,695 | A * | 8/1987 | Macovski | 378/146 |
| 4,870,667 | A * | 9/1989 | Brunnett et al. | 378/19 |
| 7,388,208 | B2 * | 6/2008 | Deych | 250/370.11 |
| 2011/0176662 | A1 * | 7/2011 | Watanabe et al. | 378/62 |
| 2012/0294421 | A1 * | 11/2012 | Mukaide et al. | 378/62 |

FOREIGN PATENT DOCUMENTS

| | | | |
|---|---|---|---|
| JP | 2001238871 | A | 9/2001 |
| JP | 2002102215 | A | 4/2002 |

(Continued)

*Primary Examiner* — Jack Berman
(74) *Attorney, Agent, or Firm* — Canon USA Inc. IP Division

(57) ABSTRACT

Provided is an X-ray imaging apparatus and an X-ray imaging method that offer an alternative for a refraction contrast method.
A first scintillator and a second scintillator are used, the first scintillator generating first fluorescent light when X-rays separated by the separating element are incident thereon, and a second scintillator generating second fluorescent light when X-rays separated by the separating element are incident thereon. The second scintillator has a fluorescence emission intensity gradient such that an amount of emitted fluorescent light changes in accordance with a change in a position at which the X-rays are incident.

11 Claims, 8 Drawing Sheets

101 102 103 104 105 106 107 108 109 110 111 112

(56) References Cited

FOREIGN PATENT DOCUMENTS

| | | | | |
|---|---|---|---|---|
| JP | 2003262673 | A | | 9/2003 |
| JP | 2008051793 | A | | 3/2008 |
| JP | 2008224661 | A | | 9/2008 |
| SU | 1519382 | A1 | * | 12/1993 |
| WO | 2008029107 | A2 | | 3/2008 |
| WO | 2008096691 | A1 | | 8/2008 |

* cited by examiner

X-RAY IMAGING APPARATUS AND X-RAY IMAGING METHOD

TECHNICAL FIELD

The present invention relates to an X-ray imaging apparatus and an X-ray imaging method using X-rays.

BACKGROUND ART

A nondestructive testing technique using an X-ray has been widely used in industry to medicine. An X-ray is electromagnetic waves having a wavelength in the range of, for example, about 1 pm to 10 nm ($10^{-12}$ to $10^{-8}$ m). An X-ray having a short wavelength (energy in the range of about 2 keV to 100 keV) are called hard X-rays, and X-rays having a long wavelength (energy in the range of about 0.1 keV to 2 keV) are called soft X-rays.

For example, according to an absorption contrast method that uses difference in X-ray absorptivity, the transmissivity for an X-ray is high and, therefore, the absorption contrast method is used for, for example, internal crack inspection of steel materials and security applications, such as baggage inspection. On the other hand, an X-ray phase imaging method detects a phase shift of X-rays caused by a detection object. The X-ray phase imaging method is effective for a detection object made of a low-density material, because absorption contrast of X-rays is not clearly formed by such a material.

Patent Literature 1 describes a refraction contrast method, which is an X-ray imaging method that uses a refraction effect caused by a detection object. To be specific, the refraction contrast method uses a microfocus X-ray source and takes an image of a detection object that is positioned at a distance from a detector. With this method, the edge of a detection object is detected in an enhanced manner owing to a refraction effect of X-rays caused by a detection object. Because the method uses the refraction effect, it is not necessary to use highly coherent X-rays such as synchrotron radiation, which distinguishes the method from many other X-ray phase imaging methods.

CITATION LIST

Patent Literature

PTL 1 Japanese Patent Laid-Open No. 2002-102215

SUMMARY OF INVENTION

Technical Problem

However, in order to obtain an edge-enhanced image of a detection object by using the refraction contrast method described in Patent Literature 1, it is necessary that the distance between a detection object and the detector be sufficiently large, because the refraction angle due to the refraction effect of X-rays caused by a detection object is very small. Therefore, the method described in Patent Literature 1 requires a large apparatus.

The present invention provides an X-ray imaging apparatus and X-ray imaging method, which offer an alternative for the refraction contrast method.

Solution to Problem

According to an aspect of the present invention, an X-ray imaging apparatus, which captures an image of a detection object using a phase shift of X-rays due to a detection object, includes a separating element that spatially separate X-rays generated by an X-ray generator; a first scintillator array including a plurality of first scintillators that are arranged, each of the first scintillators generating first fluorescent light when X-rays split by the separating element are incident thereon; a second scintillators array including a plurality of second scintillators that are arranged, each of the second scintillators generating second fluorescent light when X-rays that have passed through the first scintillator array are incident thereon, the second fluorescent light having a spectrum different from a spectrum of the first fluorescent light; and a detector configured to detect the first fluorescent light and the second fluorescent light, wherein each of the second scintillators has a fluorescence emission intensity gradient such that an amount of emitted fluorescent light changes in accordance with a change in a position at which the X-rays are incident.

Advantageous Effects of Invention

With the present invention, an X-ray imaging apparatus and X-ray imaging method, which offer an alternative for the refraction contrast method, can be provided.

DESCRIPTION OF EMBODIMENTS

In embodiments of the present invention, a scintillator array, in which scintillators each having a fluorescence emission intensity gradient are arranged, is used to obtain information regarding displacement due to a refraction effect. The term "scintillator having a fluorescence emission intensity gradient" refers to a scintillator in which the amount of fluorescent light changes in accordance with the position at which X-rays are incident. Such a scintillator can be made by continuously changing the shape or by continuously changing the amount of fluorescent light per unit volume. In this description, the term "continuously" includes the meaning of "stepwise". For example, an embodiment in which the amount of fluorescent light changes stepwise is within the scope of the present invention. In the embodiments of the present invention, scintillator having a fluorescence emission intensity gradient is used as described above, so that the problem of the above-described refraction contrast method is resolved.

The inventor of the present invention studied this imaging method and has found that, by using two or more types of scintillators having different emission spectra, a larger amount of information can be obtained in one image-taking operation than when only one type of scintillator is used.

For example, as will be described in a first embodiment, the phase gradient of a region in the XY direction can be measured in one image-taking operation by using a first scintillator having a fluorescence emission intensity gradient in the X direction and a second scintillator having a fluorescence emission intensity gradient in the Y direction.

For example, as will be described in a second embodiment, the transmittance and the phase gradient of a region can be measured in one image-taking operation by using a first scintillator that does not have a fluorescence emission intensity gradient and a second scintillator that has a fluorescence emission intensity gradient in a predetermined direction.

For example, as will be described in a third embodiment, the phase gradient in the XY direction and the transmittance can be measured by combining the first embodiment and the second embodiments.

Hereinafter, these embodiments will be described.

First Embodiment

Apparatus Configuration

Figure 1:
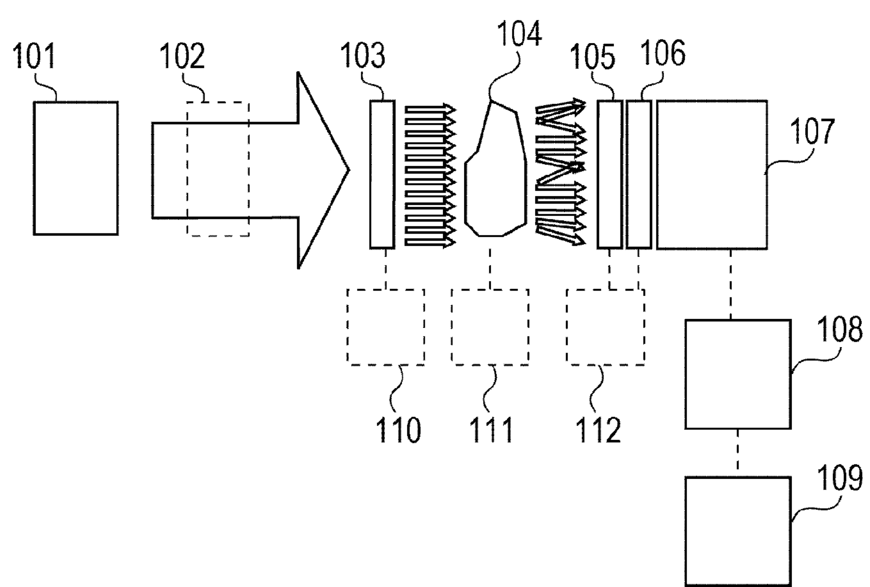
FIG. 1 is a schematic view of an X-ray imaging apparatus according to a first embodiment of the present invention.

FIG. 1 illustrates an X-ray imaging apparatus according to the present invention. FIG. 1 illustrates an X-ray source (X-ray generator unit) 101, a monochromating unit 102, an X-ray separating element 103, a detection object 104, a scintillator array 105 (first scintillator array), and a scintillator array 106 (second scintillator array), a detector (fluorescence emission intensity detecting unit) 107, a calculation unit 108, a display unit 109, a moving unit 110 for moving the X-ray separating element 103, a moving unit 111 for moving the detection object 104, and a moving unit 112 for moving the scintillator arrays 105 and 106.

The X-ray source 101 generates X-rays, the X-ray separating element 103 spatially separate the X-rays, the detection object 104 changes the phase of the X-rays, and thereby the X-rays are refracted. The refracted X-rays are incident on the scintillator arrays 105 and 106. The detector 107 detects the intensity of fluorescent light that is generated by the scintillator arrays 105 and 106. The calculation unit 108 calculates phase information of the detection object 104, such as a differential phase image and a phase image, using the intensity of fluorescent light obtained by the detector 107. The calculation unit 108 outputs the phase information, and the display unit 109 displays the phase information.

X-Ray Source and Monochromating Unit

The X-ray source 101 may be an X-ray tube, which is used in a laboratory, or a radiation light source that is used in a large synchrotron radiation facility. If X-rays emitted by the X-ray source 101 are white X-rays and monochromatic X-rays are necessary, the monochromating unit 102 may be disposed between the X-ray source 101 and the detection object 104. The monochromating unit 102 may be a monochromator combined with a slit or an X-ray multilayer mirror.

X-Ray Separating Element

The X-ray separating element 103 spatially separate the X-rays generated by the X-ray source 101. That is, the X-rays that have passed through the X-ray separating element 103 become a beam of X-rays. The X-ray separating element 103 may have a slit array with a pattern of lines and spaces, or may have holes that are arranged two-dimensionally. As long as X-rays can pass through the slits in the X-ray separating element 103, it is not necessary that the slits extend through the substrate of the optical element. The material of the X-ray separating element 103 can be selected from substances having a high X-ray absorptance, such as Pt, Au, Pb, Ta, and W. Alternatively, the material may be an alloy of these metals.

The period of the lines and spaces of the X-rays, which have been separate by the X-ray separating element 103, at the position of the detector 107 are equal to or larger than the pixel size of the detector 107. That is, the size of pixels of the detector 107, which detects fluorescent light emitted due to X-rays, is equal to or smaller than the spatial period of the X-rays that have been separated by the X-ray separating element 103.

Detection Object

Examples of the detection object 104 include a human body, a living body other than a human body, an inorganic material, and an inorganic-organic composite material. A moving unit (not shown) for moving the detection object 104 may be provided. The moving unit appropriately moves the detection object 104, so that an image of a specific part of the detection object 104 can be obtained.

Scintillator Array

Next, the scintillator arrays 105 and 106 will be described.

Figure 2:
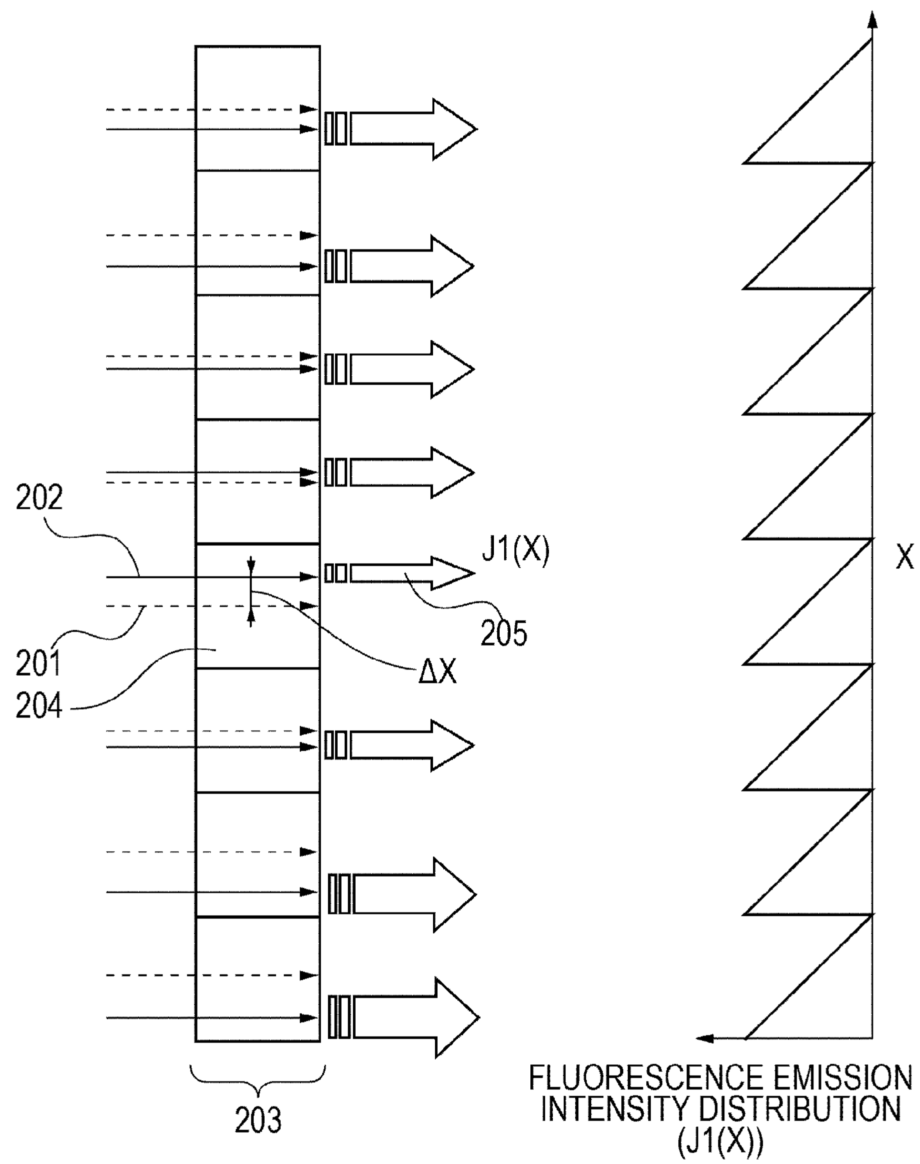
FIG. 2 is a partial schematic view of a scintillator array according to first and second embodiments of the present invention.

FIG. 2 illustrates the scintillator array 105 (first scintillator array) according to the present embodiment. FIG. 2 illustrates an optical path of reference X-rays 201 (when the detection object 104 is not present), an optical path 202 of X-rays that have been refracted by the detection object 104, a scintillator array 203 (first scintillator array) having a fluorescence emission intensity gradient, a scintillator 204 (first scintillator), and fluorescent light 205 emitted by the scintillator 204 due to the X-rays.

The scintillator 204 is made of a material that emits the fluorescent light 205 by being irradiated with X-rays. The scintillator 204 has a fluorescence emission intensity distribution that is continuous in the X direction in FIG. 2. The fluorescence emission intensity distribution that is continuous in the X direction is illustrated in the right part of FIG. 2.

For example, the fluorescence emitting material may be selected from, for example, materials that are generally used as an X-ray scintillator, such as NaI (Tl doped), CsI (Tl doped), CsI (Na doped), CsI (non-doped), LSO (Ce doped), YAP (Ce doped), and GSO (Ce doped). A fluorescence emission intensity distribution can be generated by changing the concentration of fluorescence emitting material in the scintillator 204. Alternatively, a fluorescence emission intensity distribution can be generated by changing the amount of dopant that contributes to emission. Thus, the scintillator array 105 is provided with a fluorescence emission intensity distribution J1(X) in accordance with the displacement of X-rays $\Delta X$.

The scintillator array 106 (second scintillator array) has a fluorescence emission spectrum and a fluorescence emission intensity gradient that are different from those of the scintillator array 105 (first scintillator array). That is, in contrast to the scintillator array 105, which has a fluorescence emission intensity distribution that is continuous in the X direction, the scintillator array 106 has a fluorescence emission intensity distribution that is continuous in the Y direction that is different from the X direction. Thus, the scintillator array 106 is provided with a fluorescence emission intensity distribution J2(Y) in accordance with the displacement $\Delta Y$ of X-rays.

In the scintillator described above, the amount of fluorescent light per unit volume changes in accordance with the position at which X-rays are incident. Alternatively, a scintillator having a thickness that changes in accordance with the position at which X-rays are incident may be used. That is, a scintillator array in which triangular-prism-shaped scintillators are arranged may be used.

Figure 4:
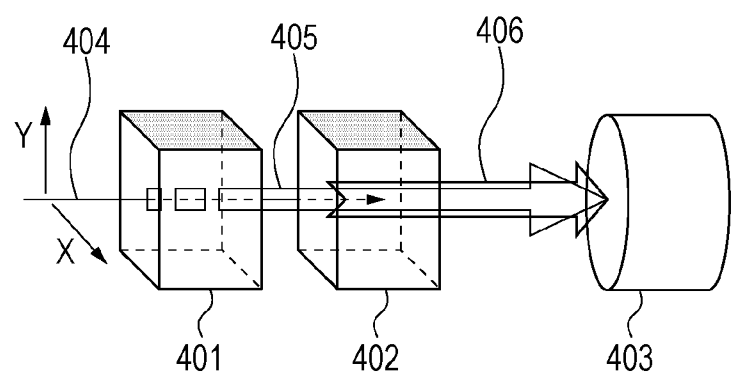
FIG. 4 is a partial schematic view of a scintillator and a detector according to the first and second embodiments of the present invention.

FIG. 4 is a conceptual diagram illustrating the configurations of the scintillator arrays 105 and 106 and the detector 107 though which a beam of X-rays separate by the X-ray separating element 103 passes. A scintillator 401 of the scintillator array 105 has a fluorescence emission intensity distribution in the X direction. A scintillator 402 of the scintillator array 106 has a fluorescence emission intensity distribution in the Y direction.

X-rays 404, which have passed through a detection object 104, excite fluorescence of the scintillators 401 and 402. Fluorescent light 405 is emitted by the scintillator 401 and has a fluorescence emission intensity distribution J1(X), and fluorescent light 406 is emitted by the scintillator 402 and has a fluorescence emission intensity distribution J2(Y). A detection element 403 of the detector 107 detects the fluorescent light 405 and the fluorescent light 406.

In order to detect the fluorescent light 405 using the detection element 403, the scintillator 402 may be capable of transmitting the fluorescent light 405. For example, CsI (Tl doped) causes fluorescence having a center emission wavelength of about 550 nm. CsI (Na doped) causes fluorescence having a center emission wavelength of about 420 nm. Because CsI (Na doped) transmits light having a wavelength of about 250 nm or longer, CsI (Na doped) transmits fluorescent light from CsI (Tl doped). Therefore, CsI (Tl doped) may be used as the scintillator 401, and CsI (Na doped) may be used as the scintillator 402. CsI (non-doped) causes fluorescence having a center emission wavelength of about 280 nm, and transmits light having a wavelength of about 350 nm or longer. Therefore, when a three-layer structure is used, scintillators may be arranged in the order of CsI (Tl doped), CsI (Na doped), and CsI (non-doped) from the side from which X-rays are incident.

Detector

The detector 107 is configured to be capable of independently detecting fluorescent light from the scintillator array 105 and fluorescent light from the scintillator array 106. For example, a solid-state imaging device in which elements having RGB color filters are arranged with a Bayer pattern may be used, and four elements RGGB can be used for the scintillator arrays 105 and 106.

As the detector 107, a camera or the like including a solid-state imaging device, such as a CCD sensor or a CMOS sensor, can be used. Such a sensor may be composed of Si for ultraviolet light and visible light, and may be composed of InSb or CdHgTe for infrared light.

The detector 107 and the scintillator array may be disposed adjacent to each other, or may be disposed with a certain distance therebetween. An optical element, such as a lens or a reflective mirror, may be disposed between the detector 107 and the scintillator array 106. By using such optical elements, X-rays that have passed through and have been scattered by the scintillator array 106 are prevented from entering the detector, whereby the S/N ratio of detection data is improved. In order to accurately measure the displacement of X-rays due to the detection object 104, the scintillator and the detection element may be integrated with each other for each pixel using a fiber plate. A band-pass filter that transmits light having the center wavelengths of the fluorescence spectra of the scintillator arrays 105 and 106 may be disposed between the scintillator arrays 105 and 106 and the detector 107.

Moving Unit

The moving units 110, 111, and 112 that respectively move the X-ray separating element 103, the detection object 104, and the scintillator arrays 105 and 106, are stepping motors or the like. Thus, the detection object 104 can be appropriately moved, so that an image of a specific part of the detection object 104 can be obtained.

Calculation Process

Next, the calculation process according to the present embodiment will be described.

Figure 3:
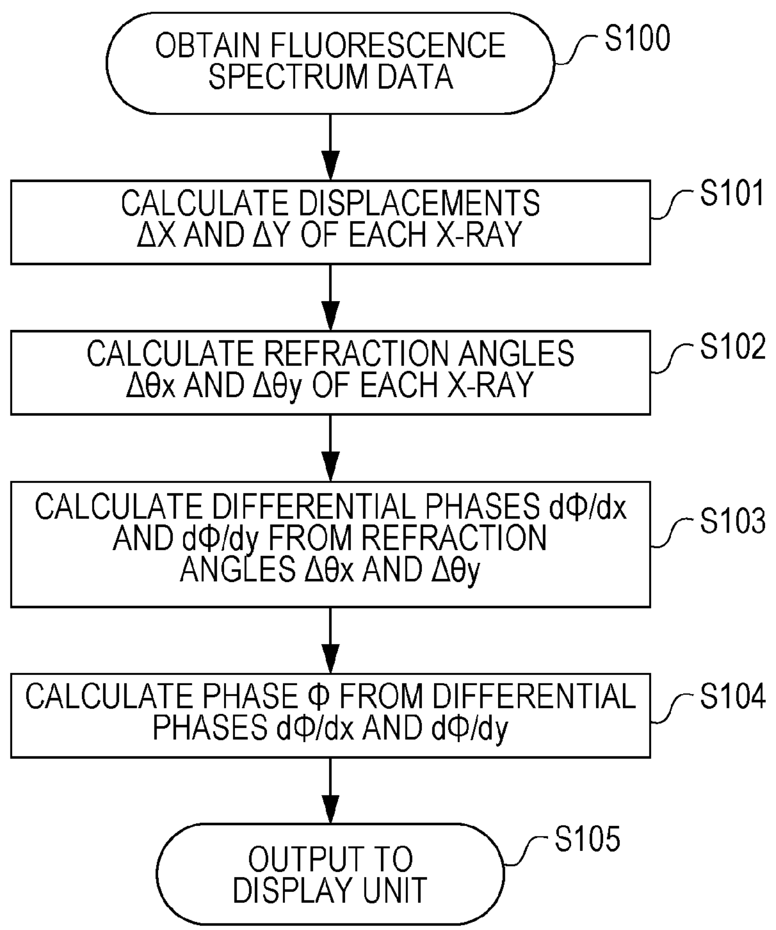
FIG. 3 is a flowchart of a calculation process according to the first embodiment of the present invention.

FIG. 3 is a flowchart of the calculation process. In step S100, the fluorescence spectra generated by the scintillator arrays 105 and 106 are acquired.

In step S101, displacement of the reference X-rays 201 (ΔX, ΔY) is calculated using intensity information of fluorescence spectrum. The displacement (ΔX, ΔY) may be calculated as the difference between the fluorescence emission intensity gradient that was determined when making the scintillator array and the fluorescence emission intensity emitted by the scintillator that is actually measured.

The displacement may be determined by referring to database that has been made beforehand. It may happen that the fluorescence emission intensity distributions (J1(X) and J2(Y)) of fluorescence spectra of the scintillators with respect to the incident position of X-rays do not have a correlation that has been planned due to production error, site-dependence of emission efficiency, and absorption of fluorescent light by the scintillator itself. Therefore, in order to accurately measure the displacement of the X-rays 404 that have been refracted, a database may be made beforehand by measuring the fluorescence emission intensity distributions (J1(X) and J2(Y)) of fluorescence spectra of the scintillators 401 and 402 with respect to the positions X and Y at which X-rays are incident. To be specific, the X-ray separating element 103 or the scintillator arrays 105 and 106 are scanned in the X-Y direction when the detection object 104 is not present, and the position at which X-rays are incident on the scintillators 401 and 402 are changed (by ΔX and ΔY). The database can be made by measuring the spectra of the fluorescent light 405 and the fluorescent light 406 emitted from the scintillators 401 and 402 by using the detection element 403.

The refraction angles (Δθx, Δθy) of each X-ray is expressed by equations (1) and (2) by using the displacement (ΔX, ΔY) and the distance Z between the detection object 104 and the scintillator arrays 105 and 106.

$$\Delta\theta x = \tan^{-1}\left(\frac{\Delta X}{Z}\right) \quad \text{[Math. 1]}$$

$$\Delta\theta y = \tan^{-1}\left(\frac{\Delta Y}{Z}\right) \quad \text{[Math. 2]}$$

In step S102, the refraction angles (Δθx, Δθy) of each X-ray is calculated by using equations (1) and (2). The refraction angles (Δθx, Δθy) and the differential phases (dϕ/dx, dϕ/dy) have relationships expressed by equations (3) and (4).

$$\frac{d\phi}{dx} = \frac{2\pi}{\lambda}\Delta\theta x \quad \text{[Math. 3]}$$

$$\frac{d\phi}{dy} = \frac{2\pi}{\lambda}\Delta\theta y \quad \text{[Math. 4]}$$

λ is the wavelength of the X-rays. When continuous X-rays are used, λ is the effective wavelength.

In step S103, the differential phases (dϕ/dx, dϕ/dy) of each X-rays are calculated by using equations (3) and (4).

In step S104, the differential phases ($d\phi/dx$, $d\phi/dy$), which are calculated as described above, are integrated in the X direction and in the Y direction to calculate a phase ($\phi$).

In step S105, the differential phases ($d\phi/dx$, $d\phi/dy$) and the phase ($\phi$), which have been thus calculated, are displayed by the display unit 109.

With the present embodiment having the above-described configuration, small changes in the refraction amount, the differential phase amount, and the phase amount caused due to the detection object 104 can be obtained. With this technology, the distance between the object and the detector may be small, so that the size of the apparatus can be reduced.

Second Embodiment

The present embodiment is configured such that the scintillator array 105 (first scintillator array), which has been described in the first embodiment, includes scintillators that are arranged, and each of the scintillators emits fluorescent light with an amount that does not change in accordance with the position at which X-rays are incident. That is, an X-ray imaging apparatus according to the present embodiment includes a scintillator array for detecting the intensity of X-rays that has passed through a detection object, which is determined by the absorption effect due to the object, and a scintillator array for detecting the displacement of X-rays due to the refraction effect. When only a scintillator array having a fluorescence emission intensity gradient is used, whether a detected change in the fluorescence emission intensity is due to the absorption effect of the object or due to the refraction effect cannot be determined. Therefore, the present embodiment is effective when absorption due to the object is not negligible.

Figure 5:
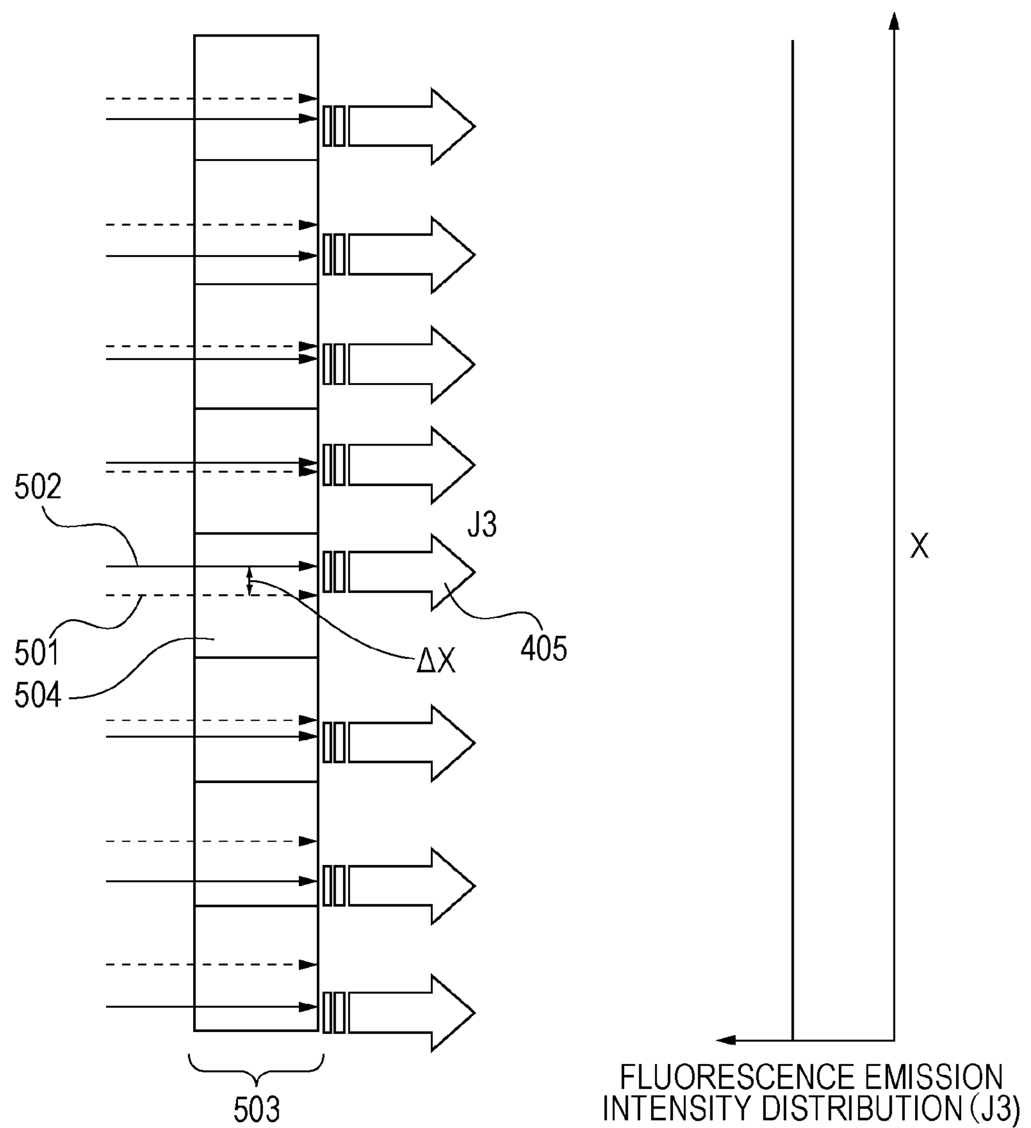
FIG. 5 is a partial schematic view of the scintillator array according to the second embodiment of the present invention.

The X-ray imaging apparatus according to the present embodiment is the same as the X-ray imaging apparatus of FIG. 1 described in the first embodiment. Referring to FIG. 5, an example configuration of the scintillator array 105 according to the present embodiment will be described. FIG. 5 is a partial view of the scintillator array 105 illustrated in FIG. 1.

Reference X-rays travel along an optical path 501 (when the detection object 104 is not present), and X-rays that have been refracted by the detection object 104 travel along an optical path 502. A scintillator array 503 includes scintillators 504 that are arranged. Each of the scintillators 504 emits fluorescent light 505 by being irradiated with X-rays, and the amount (J3) of emitted fluorescent light is uniform with respect to the position at which X-rays that have passed through the detection object 104 are incident. That is, the scintillator 504 is configured so that the amount of emitted fluorescent light does not change in accordance with the position at which X-rays are incident.

The scintillator may be made of a material the same as that of the first embodiment. In order to guide the fluorescent light emitted by the scintillator array 105 to the detector 107, the scintillator array 106 may transmit light in a wavelength band corresponding to the fluorescence spectrum of light emitted by the scintillator array 105.

In the above description, the term "a scintillator configured so that the amount of emitted fluorescent light does not change" refers to a scintillator the amount of fluorescent light emitted therefrom does not substantially change in accordance with the position at which X-rays are incident. That is, a change within the range of production error is allowed.

Next, the calculation process according the present embodiment will be described.

Figure 6:
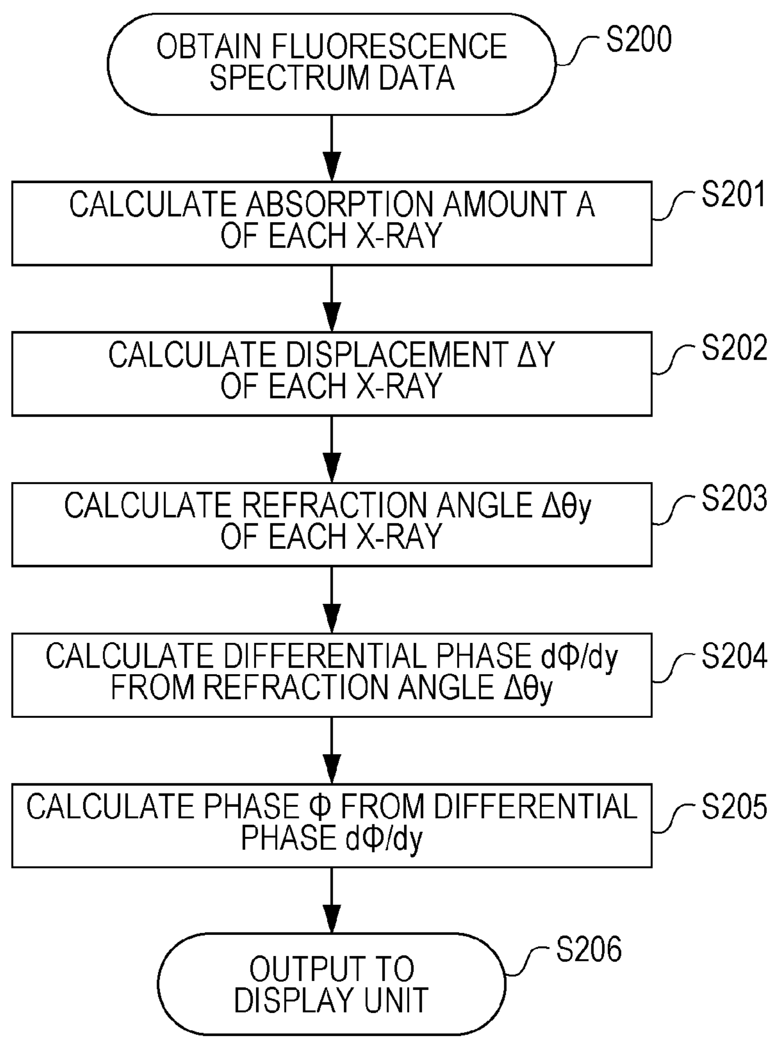
FIG. 6 is a flowchart of a calculation process according to the second embodiment of the present invention.

FIG. 6 is a flowchart of the calculation process. In step S200, the spectra of fluorescent light generated by the scintillator arrays 105 and 106 are acquired.

In step S201, the absorption amount of X-rays due to the detection object 104 is calculated. To be specific, the ratio between a fluorescence emission intensity information (J3) of the fluorescence spectrum from the scintillator array 105 obtained when the detection object 104 is not present and the fluorescence emission intensity information (J3') of the fluorescence spectrum after X-rays have passed through the detection object 104 is calculated. An absorption amount A of X-rays due to the detection object 104 is expressed by equation (5).

$$A = \frac{J3'}{J3} \qquad \text{[Math. 5]}$$

In step S202, the displacement of X-rays due to the detection object 104 is calculated. To be specific, because the fluorescence emission intensity included in the intensity information (J2'(Y)) regarding the scintillator array 106 has been reduced due to the absorption of X-rays, the intensity is corrected by dividing the intensity by the absorption amount A. By referring to the database of the intensity information (J2(Y)) of the fluorescence spectrum from the scintillator array 106, which has been obtained beforehand when the detection object 104 is not present, the displacement ($\Delta Y$) of the reference X-rays 201 is calculated using the corrected intensity information (J2'(Y)/A).

In step S203, as in the first embodiment, refraction angle ($\Delta\theta y$) of each X-ray is calculated by using equation (2).

In step S204, as in the first embodiment, the differential phase ($d\phi/dy$) of each X-ray is calculated by using equation (4).

In step S205, the phase ($\phi$) is calculated by integrating the differential phase ($d\phi/dy$), which has been calculated as described above, in the Y direction.

In step S204, the differential phase ($d\phi/dy$) and the phase ($\phi$), which have been calculated as described above, are output and displayed by the display unit 109.

With such a configuration, a small displacement of X-rays can be detected, so that the distance between the detection object 104 and the detector 107 may be small, whereby the size of the apparatus can be reduced. Because the X-ray separating element 103 is used, the differential phase amount and the phase amount are quantified. Moreover, because the scintillator array 105 is used, the absorption amount of X-rays due to the detection object 104 can be calculated, information obtained using the scintillator array 106 can be corrected, and thereby more accurate differential phase amount and phase amount can be calculated.

In the description above, the scintillator array 106 has a gradient in the Y direction. However, the scintillator array 106 may have a gradient in the X direction.

Third Embodiment

The present embodiment is a combination of the first embodiment and the second embodiment. That is, two scintillator arrays having fluorescence emission intensity gradients in two directions, which have been described in the first embodiment, and a scintillator array for measuring the absorption amount, which has been described in the second embodiment, are both used in the third embodiment.

Figure 7:
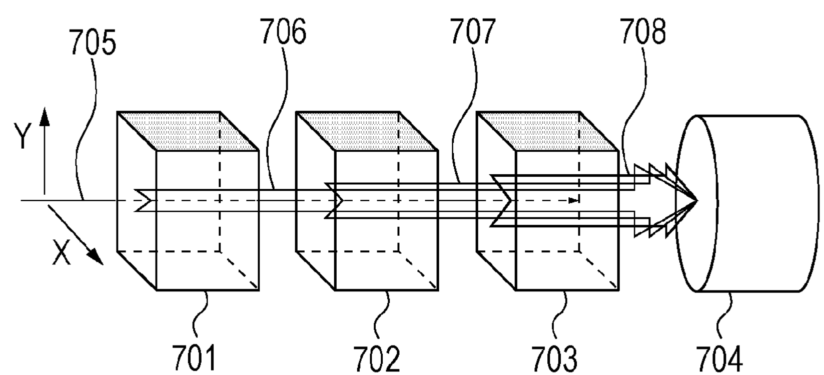
FIG. 7 is a partial schematic view of a scintillator and a detecting unit according to a third embodiment of the present invention.

FIG. 7 illustrates the configurations of the three scintillator arrays and the detector 107, which correspond to a beam of X-rays separate by the X-ray separating element 103. FIG. 7 illustrates a third scintillator 701 for measuring a transmittance (absorption amount), a first scintillator 702 having a fluorescence emission intensity gradient in the X direction, and a second scintillator 703 having a fluorescence emission intensity gradient in the Y direction. X-rays 705 that have passed through n detection object excite fluorescence in the scintillators 701, 702, and 703. Fluorescent light 706 is emitted by the scintillator 701, and has a fluorescence emission intensity distribution J3. Fluorescent light 707 is emitted by the scintillator 702, and has a fluorescence emission intensity distribution J1(X). Fluorescent light 708 is emitted by the scintillator 703, and has a fluorescence emission intensity distribution J2(Y). A detection element 704 of the detector 107 detects the fluorescent light 706, 707, and 708.

A database may be made beforehand by measuring the fluorescence emission intensity distributions (J3, J1(X), and J2(Y)) of the fluorescence spectra of the scintillators 701, 702, and 703 with respect to the positions X and Y at which X-rays are incident. Thus, the displacement of refracted X-rays 705 can be accurately measured. To be specific, by scanning the X-ray separating element 103 or the three scintillator arrays in the X-Y direction when the detection object 104 is not present, the position at which X-rays are incident on the scintillators 701, 702, and 703 can be changed (ΔX and ΔY). The database can be made by measuring the spectra of the fluorescent light 706, 707, and 708 from the scintillators 701, 702, and 703 with the detection element 704.

Therefore, by converting the absorption amount and the displacement of X-rays due to the detection object 104 to the fluorescence emission intensity distribution of fluorescence spectra and detecting the fluorescence emission intensity distribution, a small change in the refraction amount due to the detection object 104 can be obtained. By using the three scintillator arrays, the distance between the detection object and the detector can be reduced, whereby the size of the apparatus can be reduced. Next, the calculation process according to the present embodiment will be described.

Figure 8:
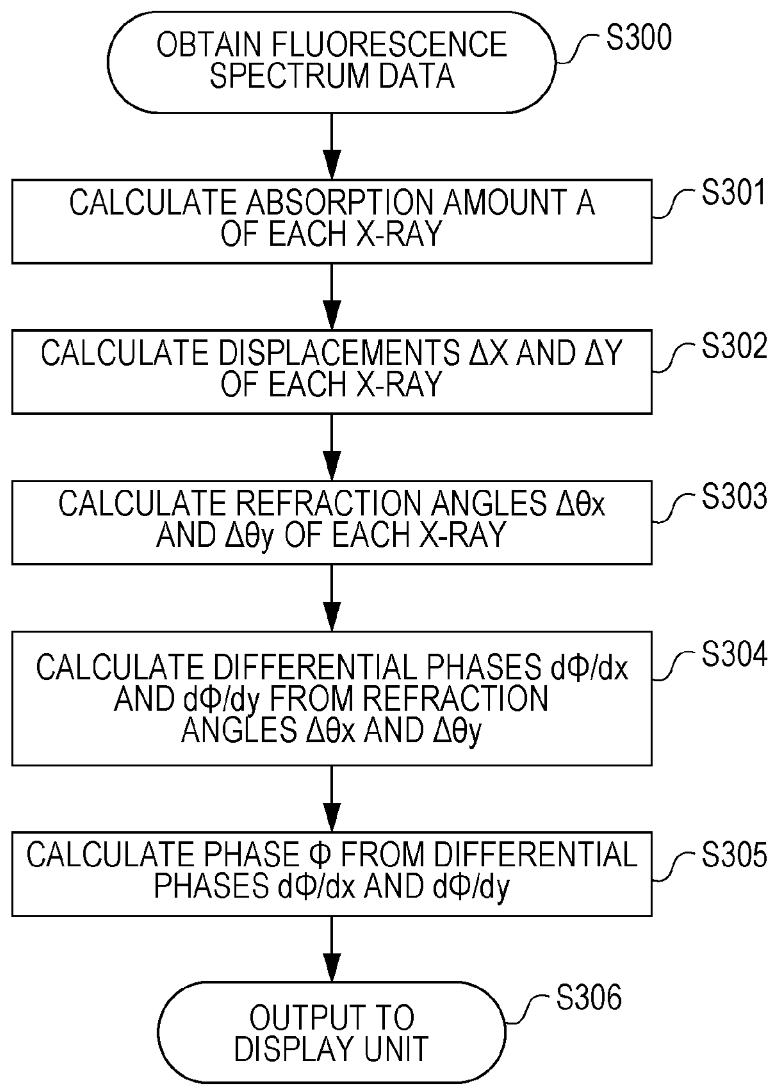
FIG. 8 is a flowchart of a calculation process according to the third embodiment of the present invention.

FIG. 8 is a flowchart of the calculation process. In step S300, fluorescence spectra generated by the three scintillator arrays are obtained.

In step S301, the absorption amount of X-rays due to the detection object 104 is calculated. To be specific, the ratio between a fluorescence emission intensity information (J3) of the fluorescence spectrum from the scintillator array 105 obtained when the detection object 104 is not present and the fluorescence emission intensity information (J3') of the fluorescence spectrum after X-rays have passed through the detection object 104 are calculated. As in the second embodiment, an absorption amount A of X-rays due to the detection object 104 is calculated by using equation (5).

In step S302, the displacement of X-rays due to the detection object 104 is calculated. To be specific, because the fluorescence emission intensity included in the fluorescence emission intensity information (J1'(X) and J2'(Y)) and obtained after X-rays have passed through the detection object 104 has been reduced due to the absorption of X-rays, the fluorescence emission intensity is corrected by dividing the fluorescence emission intensity by the absorption amount A. By referring to the database of the fluorescence emission intensity information (J1(X) and J2(Y)) regarding the fluorescence spectrum from the scintillator array 106, which has been obtained beforehand when the detection object 104 is not present, the displacement (ΔX and ΔY) of the reference X-rays 201 is calculated using the corrected intensity information (J1'(X)/A and J2'(Y)/A).

In step S303, as in the first embodiment, refraction angles (Δθx, Δθy) of each X-ray are calculated by using equation (2). In step S304, as in the first embodiment, the differential phases (dϕ/dx, dϕ/dy) of each X-ray are calculated by using equations (3) and (4). In step S305, the phase (ϕ) is calculated by integrating the differential phases (dϕ/dx, dϕ/dy), which are calculated as described above, in the X and Y directions.

Note that, in step S304, the images of the calculated differential phases (dϕ/dx, dϕ/dy), the calculated phase (ϕ), and the calculated absorption can be displaced by the display unit 109.

Other Embodiments

By using a moving unit that move the X-ray source, the separating element, the scintillator array, and the detector around the detection object 104 is synchronized manner, all projection data of the detection object can be obtained. By applying an image reconstruction method (for example, a filter back projection method) of computed tomography to the phase images of all the projection data, tomographic images of the phase (ϕ) are obtained. Thus, three-dimensional images of the differential phase images (dϕ/dx, dϕ/dy) and the phase image (ϕ) can be constructed. By using a scintillator in which the amount of fluorescent light does not change with respect to the position at which X-rays are incident, a three-dimensional image of the absorption image can be constructed.

The detection object may be rotated so as to obtain a projection data, instead of rotating the separating element, the scintillator array, and the detector.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-049313, filed Mar. 5, 2010, which is hereby incorporated by reference herein in its entirety.

The invention claimed is:

1. An X-ray imaging apparatus for capturing an image of an object using a phase shift of X-rays due to the detection object, the apparatus comprising:

a separating element that spatially separate X-rays generated by an X-ray generator;

a first scintillator array including a plurality of first scintillators that are arranged, each of the first scintillators generating first fluorescent light when X-rays separated by the separating element are incident thereon;

a second scintillator array including a plurality of second scintillators that are arranged, each of the second scintillators generating second fluorescent light when X-rays that have passed through the first scintillator array are incident thereon, the second fluorescent light having a spectrum different from a spectrum of the first fluorescent light; and a detecting unit configured to detect the first fluorescent light and the second fluorescent light, wherein each of the second scintillators has a fluorescence emission intensity gradient such that an amount of emitted fluorescent light changes in accordance with a change in a position at which the X-rays are incident.

2. The X-ray imaging apparatus according to claim 1, wherein each of the first scintillators has a fluorescence emission intensity gradient such that an amount of fluorescent light emitted due to the X-rays changes in accordance with a position at which the X-rays are incident, and wherein a direction of the fluorescence emission intensity gradient of the first scintillator is different from a direction of the fluorescence emission intensity gradient of the second scintillator.

3. The X-ray imaging apparatus according to claim 1, wherein each of the first scintillators is configured so that an amount of fluorescent light emitted due to the X-rays does not change in accordance with a change in a position at which the X-rays are incident.

4. The X-ray imaging apparatus according to claim 1, further comprising:

a third scintillator array including a plurality of third scintillators that are arranged, each of the third scintillators generating third fluorescent light when X-rays separate by the separating element are incident thereon, wherein a spectrum of the third fluorescent light is different from the spectrum of the first fluorescent light and the spectrum of the second fluorescent light, and wherein the detecting unit is configured to detect the third fluorescent light.

5. The X-ray imaging apparatus according to claim 1, further comprising:

a calculating unit configured to calculate a differential phase image or a phase image of the detection object using an intensity of fluorescent light detected by the detecting unit.

6. The X-ray imaging apparatus according to claim 1, wherein a thickness of each of the second scintillators continuously changes in a direction perpendicular to a direction of incident X-rays or an amount of fluorescent light emitted per unit volume of each of the second scintillators continuously changes.

7. The X-ray imaging apparatus according to claim 2, wherein a thickness of each of the first scintillators continuously changes in a direction perpendicular to a direction of incident X-rays or an amount of fluorescent light emitted per unit volume of each of the first scintillators continuously changes.

8. The X-ray imaging apparatus according to claim 3, wherein a thickness of each of the first scintillators is uniform in a direction perpendicular to a direction of incident X-rays or an amount of fluorescent light emitted per unit volume of each of the first scintillators is uniform.

9. An X-ray imaging method used in an X-ray imaging apparatus for capturing an image of a detection object using a phase shift of X-rays due to the detection object, the method comprising:

irradiating a detection object with X-rays that have been spatially separated;

making the X-rays incident on a first scintillator array and a second scintillator array, the first scintillator array including a plurality of first scintillators that are arranged, each of the first scintillators generating first fluorescent light, the second scintillator array including a plurality of second scintillators that are arranged, each of the second scintillators generating second fluorescent light when X-rays that have passed through the first scintillator array are incident thereon, the second fluorescent light having a spectrum different from a spectrum of the first fluorescent light; and detecting the first fluorescent light and the second fluorescent light, wherein each of the second scintillators has a fluorescence emission intensity gradient such that an amount of emitted fluorescent light changes in accordance with a change in a position at which the X-rays are incident.

10. The X-ray imaging method according to claim 9, wherein each of the first scintillators has a fluorescence emission intensity gradient such that an amount of fluorescent light emitted due to the X-rays changes in accordance with a position at which the X-rays are incident, and wherein a direction of the fluorescence emission intensity gradient of the first scintillator is different from a direction of the fluorescence emission intensity gradient of the second scintillator.

11. The X-ray imaging method according to claim 9, wherein each of the first scintillators is configured so that an amount of fluorescent light emitted due to the X-rays does not change in accordance with a change in a position at which the X-rays are incident.

* * * * *